(12) United States Patent
Fine et al.

(10) Patent No.: US 8,011,258 B2
(45) Date of Patent: Sep. 6, 2011

(54) EXPLOSIVE RESIDUE SAMPLING

(75) Inventors: David H. Fine, Lincoln, MA (US); Ravi K. Konduri, Heathrow, FL (US); Freeman W. Fraim, Lexington, MA (US); George Jarvis, Arlington, MA (US)

(73) Assignee: L-3 Communications CyTerra Corporation, Waltham, MA (US)

( * ) Notice: Subject to any disclaimer, the term of this patent is extended or adjusted under 35 U.S.C. 154(b) by 1038 days.

(21) Appl. No.: 10/928,730

(22) Filed: Aug. 30, 2004

(65) Prior Publication Data
US 2005/0081655 A1   Apr. 21, 2005

Related U.S. Application Data

(60) Provisional application No. 60/498,323, filed on Aug. 28, 2003.

(51) Int. Cl.
*G01N 1/04* (2006.01)
(52) U.S. Cl. .................................................. 73/864.71
(58) Field of Classification Search ............... 73/864.71, 73/864.72
See application file for complete search history.

(56) References Cited

U.S. PATENT DOCUMENTS

| | | | |
|---|---|---|---|
| 3,091,967 A * | 6/1963 | Hurdlow et al. | 73/864.71 |
| 3,554,039 A * | 1/1971 | Braun | 73/864.71 |
| 3,841,973 A * | 10/1974 | Wilkins et al. | 73/864.71 |
| 3,897,688 A * | 8/1975 | Meserol et al. | 73/864.71 |
| 4,848,165 A * | 7/1989 | Bartilson et al. | 73/864.71 |
| 5,859,375 A | 1/1999 | Danylewych-May | |
| 5,939,647 A * | 8/1999 | Chinn et al. | 73/864.71 |
| 5,988,002 A * | 11/1999 | Danylewych-May et al. | 73/864.71 |
| 6,382,036 B1 * | 5/2002 | Woodmansee | 73/864.71 |
| 2005/0101027 A1 * | 5/2005 | Haas | 436/109 |

* cited by examiner

*Primary Examiner* — Hezron Williams
*Assistant Examiner* — Nashmiya Fayyaz
(74) *Attorney, Agent, or Firm* — Fish & Richardson P.C.

(57) ABSTRACT

In one aspect, an apparatus includes a head configured to receive a pad for sampling explosive residue on a surface and a feedback system coupled to the head. The feedback system is configured to indicate when a pressure applied by the head is greater than a minimum threshold value. In another aspect, an apparatus includes a head configured to receive a pad and rotate to apply a shear force to the pad for sampling explosive residue on a surface. The apparatus includes a feedback system coupled to the head, which is configured to restrict the shear force applied by the head to be within a predetermined range. In another aspect, a method includes applying pressure to a pad to sample explosive residue on a surface, sensing the pressure applied to the pad, and providing an indication of when the pressure applied to the pad is greater than a threshold value.

36 Claims, 5 Drawing Sheets

EXPLOSIVE RESIDUE SAMPLING

PRIORITY

This application claims priority from U.S. Provisional Application 60/498,323, which was filed Aug. 28, 2003 and is incorporated by reference.

TECHNICAL FIELD

This invention relates to sampling for the presence of explosives and other materials.

BACKGROUND

Screening carry-on and checked luggage for trace explosive residues is a common airport security practice. Sampling for trace explosive residue generally is conducted by wiping over sample surfaces, such as latches, handles, straps and zippers, with a paper or plastic detection pad that is attached to a plastic stick about one foot long. The pad picks up trace explosive particles left by fingerprints on the surfaces. The pad is then analyzed using an explosive detection system (EDS), also known as an explosive trace detector (ETD).

SUMMARY

In one aspect, an apparatus includes a head configured to receive a pad for sampling explosive residue on a surface and a feedback system coupled to the head. The feedback system is configured to indicate when a pressure applied by the head is greater than a minimum threshold value.

Implementations may include one or more of the following features.

The feedback system may include a pressure sensor for sensing the pressure applied by the head to the surface. The pressure sensor may include a pressure transducer or a spring. The feedback system may include a processor configured to compare the applied pressure to the minimum threshold value. The minimum threshold value may be selected to reduce false negative readings. The minimum threshold value may be between about 1 psi and about 5 psi, particularly about 3 psi.

The feedback system may further include an indicator that indicates when the applied pressure is greater than the minimum threshold value. The indicator may include, for example, a visual indicator, an audible indicator, or a tactile indicator, such as a switching element that activates rotation of the head. The feedback system may include an indicator than indicates when the applied pressure is less than the minimum threshold value.

The feedback system may be configured to indicate when the applied pressure is less than or greater than a maximum threshold value, for example, about 5 psi.

The head may be rotatable and the feedback system may be configured to indicate when a shear force applied by the head is within a predetermined range. The apparatus may include a motor for rotating the head. The feedback system may include a tachometer for measuring the rotational speed of the head. The feedback system may cause the motor to rotate the head at a speed between about 100 rpm and about 300 rpm. The feedback system may be configured to shut off the motor when the rotational speed of the head exceeds about 300 rpm or is less than about 100 rpm. The head may be rotatable and the feedback system may be configured to indicate when a shear force applied by the head is outside a predetermined range.

The feedback system may include a timer that senses a length of time that the pressure is applied by the head. The feedback system may include an indicator for indicating when the length of time is greater than or less than a predetermined time value, for example, about 10 seconds. The may include a handle having an axis and coupled to the head to allow a user to apply the pressure to the head. The head may be offset from the axis or may be aligned with the axis. The head also may be arc-shaped to rotate orbitally about the axis.

In another aspect, an apparatus includes a head configured to receive a pad and rotate to apply a shear force to the pad for sampling explosive residue on a surface. The apparatus also includes a feedback system coupled to the head. The feedback system is configured to restrict the shear force applied by the head to be within a predetermined range.

In another aspect, a method includes applying pressure to a pad to sample explosive residue on a surface, sensing the pressure applied to the pad, and providing an indication of when the pressure applied to the pad is greater than a threshold value. Implementations may include one or more of the following features. Providing an indication may include applying a shear force to the pad. Applying a shear force may include rotating the pad. The method may include indicating if the shear force is within a predetermined range.

The details of one or more implementations are set forth in the accompanying drawings and the description below. Other features and advantages will be apparent from the description and drawings, and from the claims.

DETAILED DESCRIPTION

Figure 1:
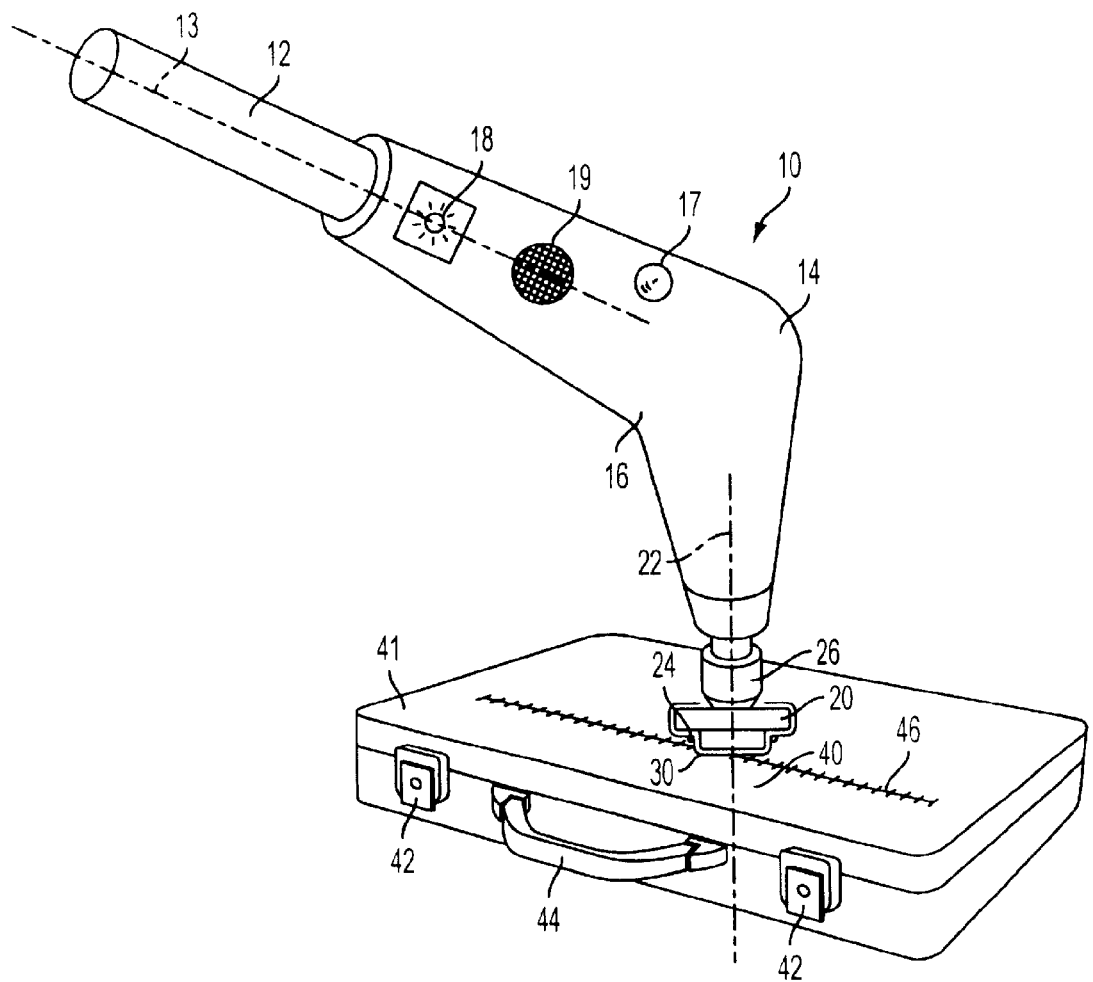
FIG. 1 is a perspective view of a sampling wand.

Referring to FIG. 1, an automated, pressure-activated, sampling wand 10 reduces the variability inherent in manual trace explosive sampling due to inconsistencies in applied pressure, shearing force and sampling time, which could cause false-negative readings (i.e., failing to detect explosives). Using wand 10, the operator can collect more consistent samples, irrespective of the operator's level of concentration, arm and muscle strength, and/or fatigue.

Wand 10 includes a handle 12, a housing 14, and a head 20. Head 20 receives a paper or plastic detection pad 30 for sampling trace explosive residue on a surface 41, e.g., a latch 42, handle 44, or zipper 46, of a bag 40. The operator collects a sample from surface 41 by manipulating handle 12 to apply pressure to head 20 against surface 41 and to slide head 20 across surface 41.

Head 20 is rotatably coupled to housing 14 by a rotatable shaft 26, which in turn is coupled to a motor (not shown) located inside housing 14. The motor is activated to rotate head 20 when the operator presses head 20 against surface 41 with sufficient force to obtain a sample. Thus, rotation of head 20 assists in obtaining a sample by application of a shearing force. As the torque required to turn head 20 is not large, the required motor power is small, which, in turn, allows for the use of batteries as the power source. For ergonomic design reasons, handle 12 has a longitudinal axis 13 and rotatable head rotates about an axis 22 that is offset from axis 13. The angle of the offset is determined by the angle of bend 16 in housing 12.

Housing 14 also includes a light 18 for providing a visual indication and a speaker 19 for providing an audible alarm, as described in more detail below. In addition, housing 14 includes an on-off switch 17 that allows the operator to turn wand 10 on or off. Apart from on-off switch 17, wand 10 has no user accessible controls, which makes wand 10 tamper-resistant.

Figure 2:
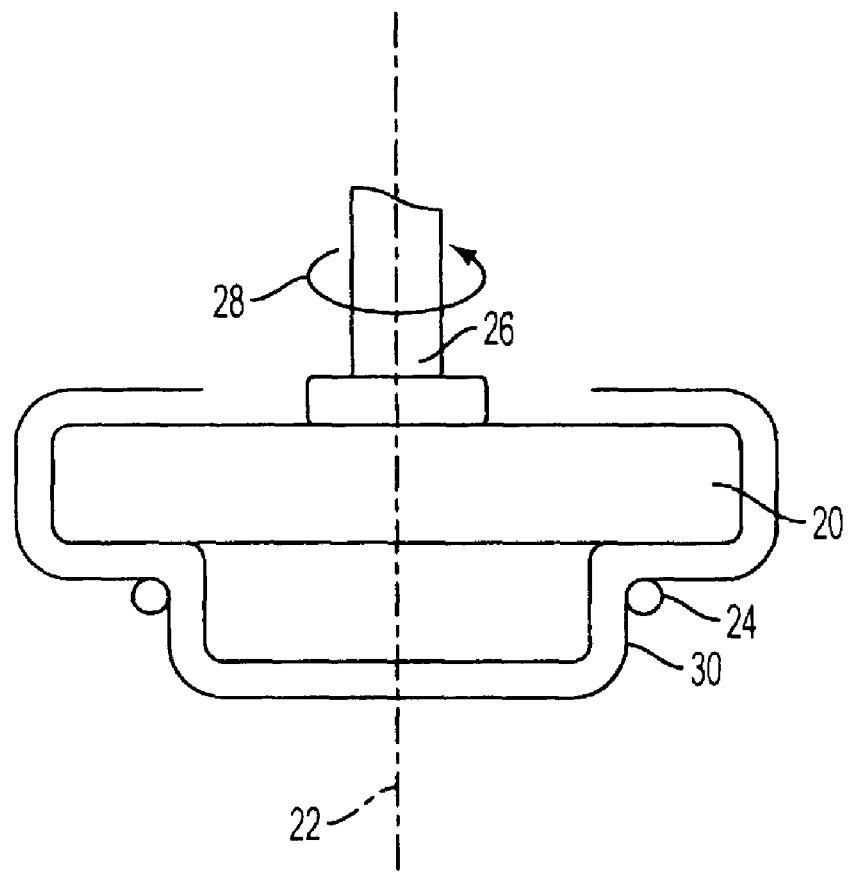
FIG. 2 is a side view of a pad attached to a head of the sampling wand of FIG. 1.

Referring also to FIG. 2, pad 30 is wrapped about head 20 and is affixed to head 20 by a metal or plastic clip 24. Wand 10 can receive any type of pad that is used with known EDSs. Wand 10 may be used with a variety of EDSs, including those approved by the United States Transportation Security Administration (TSA), such as the Ionscan 400B marketed by Smiths Detection of Pine Brook, N.J., the EGIS II and EGIS III marketed by Thermo Electron Corp. of Franklin, Mass., and the ITEMISER marketed by GE Ion Track of Wilmington, Mass. Sample pads can be re-used multiple times until they degrade or are contaminated by trace explosive material.

Figure 3:
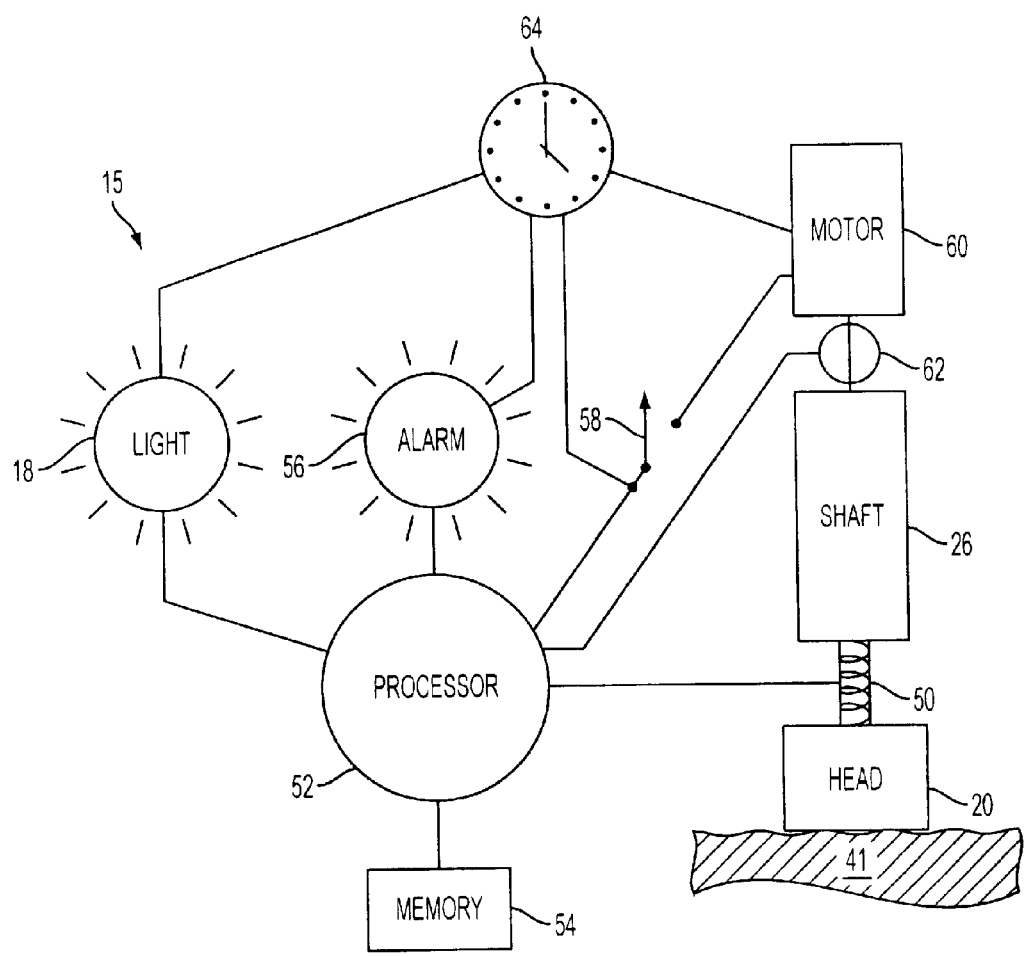
FIG. 3 is a schematic diagram of a feedback control system of the sampling wand of FIG. 1.

Referring to the schematic diagram in FIG. 3, wand 10 includes a feedback system 15 that reduces operator-dependant variability and increases the consistency of the sample taken by indicating when the pressure applied by head 20 to surface 41 is greater than a minimum threshold value (to obtain a consistent sample and avoid false negative readings) and is less than a maximum threshold value (to inhibit damage to the surface or to pad 30). Feedback system 15 includes a pressure sensor 50, e.g., a pressure transducer or a spring, for sensing the pressure applied by head 20 to surface 41. Pressure sensor 50 is coupled to a processor 52 that is configured to compare the sensed pressure to minimum and maximum threshold values stored in a memory 54.

When the processor 52 determines that the sensed pressure is greater than the minimum threshold value and/or less than the maximum threshold value, processor 52 activates a tactile indication by toggling a switch 58 to activate motor 60 to rotate head 20, activates a visual indication, such as light 18, and/or activates an audible indication, such as alarm 56. In other implementations, processor 52 toggles switch 58 to shut off motor 60, activates light 18, and/or activates alarm 56 when the sensed pressure is less than the minimum threshold value or greater than the maximum threshold value. In other implementations, only a minimum threshold value is employed.

To determine the appropriate minimum and maximum threshold pressure values, an experiment was conducted in which fingerprints were deposited on a glass plate and the plate was placed on a small laboratory electronic scale. A relatively sturdy paper (e.g., a business card) was used as a surrogate for pad 30 to attempt to remove a sample of residue from the fingerprint. Different pressures were applied and measured by the readings on the electronic scale. Following sampling, the mirror was visually inspected after each wipe to determine the efficiency of the fingerprint removal. It was found that an applied pressure of about 3 to about 5 lbs per sq. inch (psi) was needed to remove the fingerprint from the glass. A pressure of about 1 or 2 psi was judged to be inadequate for consistent sampling. In practice, it is difficult for an ordinary person to maintain about 5 psi for a time interval even as short as 10 seconds, due to muscle fatigue. An ordinary person can maintain about 3 psi for 30 or more seconds without much difficulty. It also was determined that applying a pressure of greater than 5 psi could result in damage to the sampling medium or to the surface. Accordingly, in one particular implementation, the minimum threshold pressure value is about 3 psi and the maximum threshold pressure value is about 5 psi.

Feedback system 15 also reduces operator-dependant variability and increases the consistency of the sample taken by indicating when a shear force applied by the rotation of head 20 is within a predetermined range for consistent sampling. Feedback system 15 includes a device for measuring the rate of rotation of head 20, such as, for example, a tachometer 62 that is coupled to processor 52. Processor 52 compares the rotational speed of head 20 and compares that speed to a minimum and maximum speed stored in memory 54. The maximum and minimum speed correspond to the minimum and maximum shear force that it is desired to apply with head 20. Through a feedback loop, the processor 52 adjusts the speed of motor 60 to maintain the speed of head 20 within the desired range of speeds. In addition, if the measured speed is less than the minimum speed or greater than the maximum speed, the processor 52 may trigger the illumination of light 18, the sounding of audible alarm 56, or the opening of switch 58 to shut off motor 60. In other implementations, the processor 52 triggers illumination of light 18 or the sounding of alarm 56 when the measured speed is greater than the minimum speed and/or less than the maximum speed.

The predetermined range of speed of head 20 was determined in an experiment in which fingerprints were deposited on a mirror and the mirror was placed on an electronic laboratory scale. A one square-inch piece of sampling paper was attached to the head of a motorized rotary tool and the tool was applied to the surface of the mirror with a force of about 3 psi. Experiments with varying rotary speeds showed that a rotary speed of about 60 to about 300 revolutions per minute (rpm), and preferably about 100 to 300 rpm, generates a shear force that is sufficient to collect a consistent sample. It also was determined that it takes approximately five rotations at these speeds to remove a fingerprint from a smooth surface.

Feedback system 15 also reduces operator-dependant variability and increases the consistency of the sample taken by indicating and controlling the length of time during which a sample is taken. Feedback system 15 includes a timer 64 that measures the time during which a sample is taken and compares that time to a predetermined length of time. If the sample is taken for too short and/or too long a period of time, the timer 64 indicates this to the user, such as by causing light 18 to be illuminated and/or alarm 56 to be sounded. Once the desired time has expired, the timer 64 toggles switch 58 to disable motor 60 and stop the rotation of head 20. In the experiments discussed above, the length of time that is desired for taking a sample was determined to be about 10 seconds, for the pressure and rotation speeds set forth above. Increasing the applied pressure or the applied shear force would reduce the number of rotations required, and thus the desired sampling time.

Wand 10, including feedback control system 15, is built primarily from off-the-shelf components, such as an electric motor, bearings, a pressure transducer, and simple integrated circuits, all of which are integrated into a small plastic housing. Off-the-shelf components increase the expected reliability of the final product, while making it cost-effective.

In use, the operator attaches pad 30 to head 20 using clip 24. The operator then manipulates handle 12 to cause head 20 to apply pressure to surface 41. When the pressure applied by the operator to head 20 exceeds the minimum threshold value, motor 60 will automatically rotate head 20. An audible and/or visual alarm also may be provided to the operator. The operator then manipulates handle 12 to slide head 20 across surface 41 to collect a sample. Once a sufficient time has elapsed to collect the sample, motor 60 automatically shuts off and the operator lifts the head off of surface 41. The operator then removes pad 30 and analyzes pad 30 for explosive residue in an ETD machine. While the operator is collecting the sample, if the operator applies too little or too much pressure, the motor will shut off. An audible and/or visual indicator also may be provided to the operator. Similarly, if the shear force applied by head 20 is outside a predetermined range, the motor will shut off. An audible and/or visual indicator also may be provided to the operator.

Figure 4:
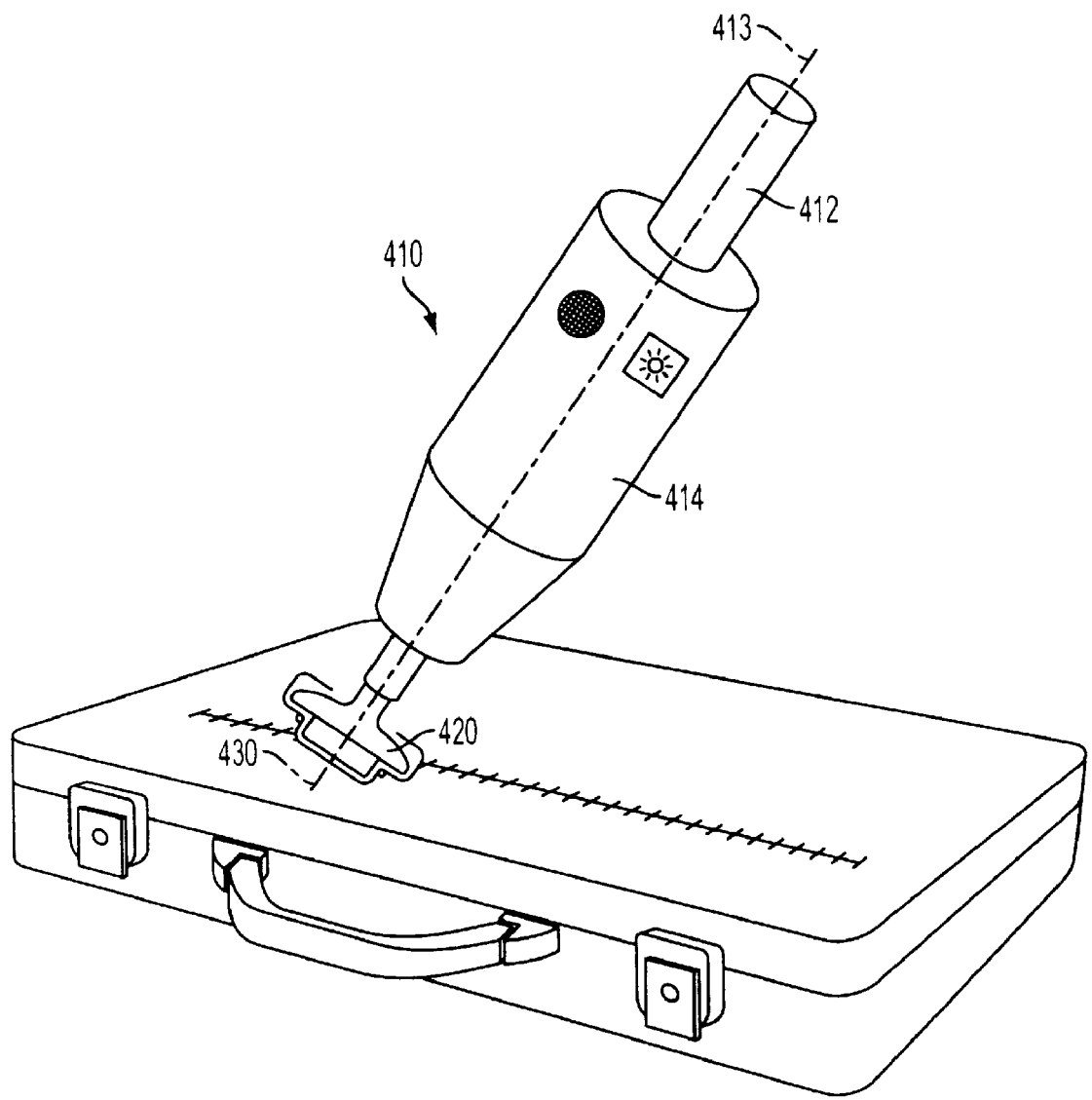
FIG. 4 is a perspective view of a second implementation of a sampling wand.

Referring to FIG. 4, in another implementation, a wand 410 includes a head 420 that rotates about an axis 430 that is aligned with an axis 413 of a handle 412 and a housing 414.

Figure 5:
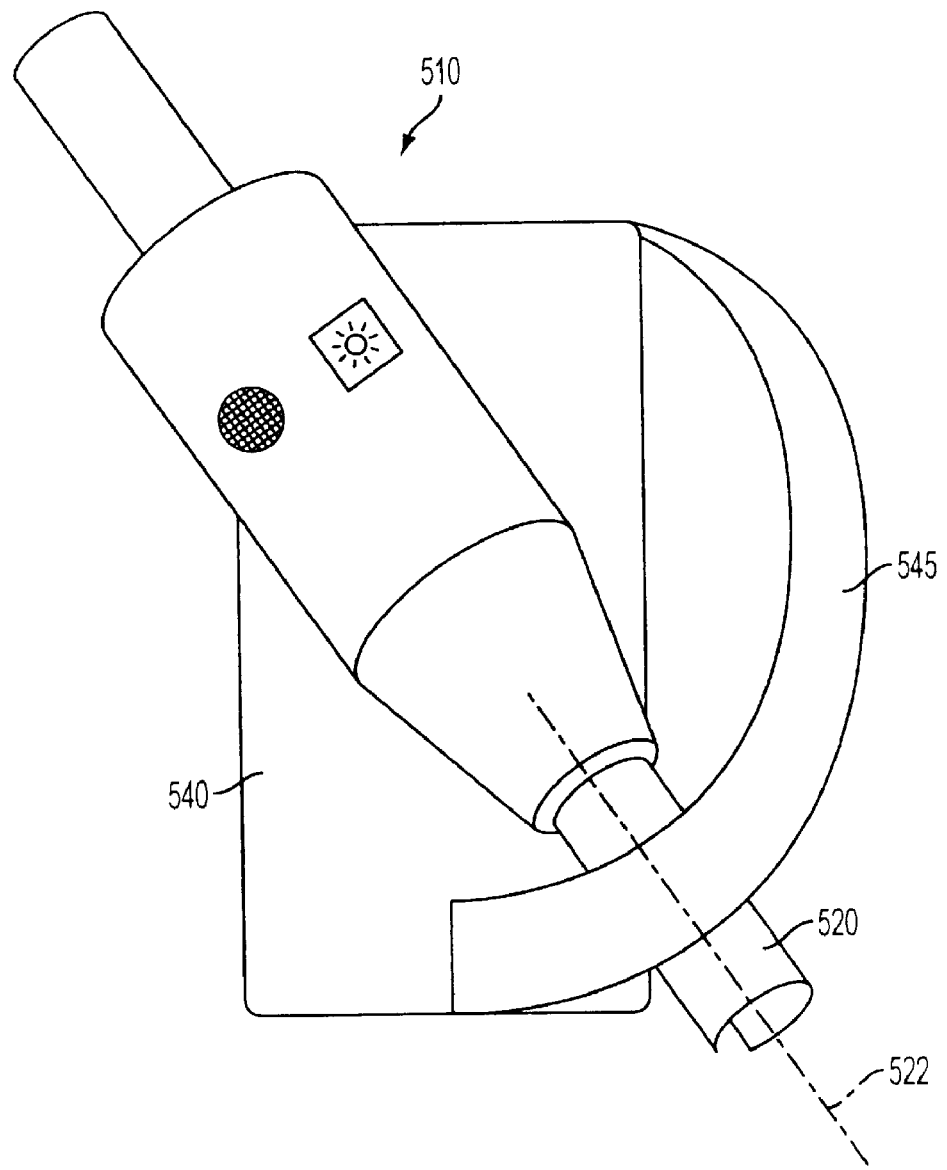
FIG. 5 is a perspective view of a third implementation of a sampling wand.

Referring to FIG. 5, in yet another implementation, a wand 510 includes a head 520 that is arc-shaped so that it rotates orbitally around axis 522 to facilitate obtaining samples from a strap 545 of a handbag 540.

A number of implementations have been described. Nevertheless, it will be understood that various modifications may be made. For example, the angle of the housing may be adjustable. The pad may be attached to the head by other mechanisms, such as friction fit, staples, or suction. There may be more than one light, different color lights, or more than one type of audible alarm for indicating various of the events described above. The feedback system may be formed by an ordinary electrical circuit or an integrated circuit. Instead of the head rotating to impart the shear force, the head can oscillate or vibrate. These and other implementations are within the scope of the following claims.

What is claimed is:

1. An apparatus comprising:
a head configured to receive a pad and rotate to apply a shear force to the pad for sampling explosive residue on a surface;
a feedback system coupled to the head, the feedback system configured to restrict the shear force applied by the head to be within a predetermined range, wherein the head is configured to apply pressure to the pad, and the feedback system includes a pressure sensor for sensing the pressure applied by the head to the surface; and
a processor coupled to the pressure sensor, the processor configured to:
determine that a pressure sensed by the pressure sensor is greater than a minimum threshold value and less than a maximum threshold value,
activate a motor to rotate the head based on the determination,
determine a duration of time during which the head applies pressure to the pad,
compare the determined duration to a preset length of time, and
deactivate the motor if the determined duration is equal to or greater than the preset length of time.

2. The apparatus of claim 1, wherein the processor is further configured to:
deactivate the motor if a pressure sensed by the pressure sensor is below the minimum threshold value, and
reactivate activation of the motor when the pressure sensed by the pressure sensor is greater than the minimum threshold value and less than the maximum threshold value.

3. The apparatus of claim 1 wherein the pressure sensor includes a pressure transducer.

4. The apparatus of claim 1 wherein the pressure sensor includes a spring.

5. The apparatus of claim 1 wherein the processor is further configured to compare the applied pressure to a minimum threshold value.

6. The apparatus of claim 5 wherein the minimum threshold value is selected to reduce false negative readings.

7. The apparatus of claim 5 wherein the minimum threshold value is between about 1 psi and about 5 psi.

8. The apparatus of claim 7 wherein the minimum threshold value is about 3 psi.

9. The apparatus of claim 1 wherein applying shear force to the pad comprises applying pressure to the pad, and the feedback system further comprises an indicator that indicates when the applied pressure is greater than the minimum threshold value.

10. The apparatus of claim 9 wherein the indicator includes one or more of a visual indicator, an audible indicator, or a tactile indicator.

11. The apparatus of claim 1, wherein the feedback system further comprises an indicator that indicates when the shear force is outside of the predetermined range.

12. The apparatus of claim 1 further comprising:
the motor for rotating the head;
a device for measuring a rate of rotation of the head; and
wherein the processor is further configured to monitor the rate of rotation of the head.

13. The apparatus of claim 10 wherein the indicator is a tactile indicator, and the tactile indicator includes a switching element that activates rotation of the head.

14. The apparatus of claim 1 wherein the feedback system further comprises an indicator that indicates when the applied pressure is less than a minimum threshold value.

15. The apparatus of claim 1 wherein the feedback system is further configured to indicate when the applied pressure is greater than a maximum threshold value.

16. The apparatus of claim 1 wherein the feedback system is further configured to indicate when the applied pressure is less than a maximum threshold value.

17. The apparatus of claim 16 wherein the maximum threshold value is about 5 psi.

18. The apparatus of claim 12, further comprising an electronic memory coupled to the processor, and wherein to monitor the rate of rotation of the head, the processor is configured to compare the rate of rotation of the head to one or more of a minimum or maximum rate of rotation stored in the electronic memory.

19. The apparatus of claim 1 further comprising the motor for rotating the head.

20. The apparatus of claim 19 wherein the feedback system includes a tachometer for measuring the rotational speed of the head.

21. The apparatus of claim 19 wherein the feedback system causes the motor to rotate the head at a speed between about 100 rpm and about 300 rpm.

22. The apparatus of claim 19 wherein the feedback system is configured to shut off the motor when the rotational speed of the head exceeds about 300 rpm.

23. The apparatus of claim 19 wherein the feedback system is configured to shut off the motor when the rotational speed of the head is less than about 100 rpm.

24. The apparatus of claim 18, wherein the predetermined range of shear force is defined by a first rate of rotation and a second rate of rotation, and a minimum and maximum speed stored in the electronic memory respectively correspond to the first rate of rotation and the second rate of rotation.

25. The apparatus of claim 1 wherein the feedback system includes a timer that senses the duration of time that the pressure is applied by the head.

26. The apparatus of claim 25 wherein the feedback system includes an indicator for indicating when the duration of time is greater than or less than the preset length of time.

27. The apparatus of claim 26 wherein the preset length of time is about 10 seconds.

28. The apparatus of claim 1 further comprising a handle having an axis and coupled to the head to allow a user to apply the pressure to the head.

29. The apparatus of claim 28 wherein the head is offset from the axis.

30. The apparatus of claim 28 wherein the head is aligned with the axis.

31. The apparatus of claim 28 wherein the head is arc-shaped to rotate orbitally about the axis.

32. The apparatus of claim 18, wherein the processor is further configured to adjust the rate of rotation of the motor to maintain the rate of rotation within the minimum and maximum rate of rotation.

33. The apparatus of claim 18, wherein the processor is further configured to trigger an alarm when the rate of rotation of the head is greater than the maximum rate of rotation or less than the minimum rate of rotation.

34. The apparatus of claim 18, wherein the processor is further configured to present one or more of a visual indicator or an audio indicator when the rate of rotation of the head is greater than the maximum rate of rotation or less than the minimum rate of rotation.

35. The apparatus of claim 18, wherein the processor is further configured to cause the head to stop rotating when the rate of rotation of the head is greater than the maximum rate of rotation or less than the minimum rate of rotation.

36. The apparatus of claim 1, wherein the feedback system causes the motor to rotate the head at a speed between about between about 60 rpm and about 300 rpm.

* * * * *

UNITED STATES PATENT AND TRADEMARK OFFICE
CERTIFICATE OF CORRECTION

PATENT NO. : 8,011,258 B2  Page 1 of 1
APPLICATION NO. : 10/928730
DATED : September 6, 2011
INVENTOR(S) : David H. Fine et al.

It is certified that error appears in the above-identified patent and that said Letters Patent is hereby corrected as shown below:

In column 8, line 16, in claim 36, before "60" delete "between about".

Signed and Sealed this
Fourteenth Day of February, 2012

David J. Kappos
*Director of the United States Patent and Trademark Office*